US006395920B1

(12) United States Patent
Bauer et al.

(10) Patent No.: US 6,395,920 B1
(45) Date of Patent: *May 28, 2002

(54) PROCESS FOR PREPARING SUBSTITUTED ACETALS OF MALONDIALDEHYDE

(75) Inventors: Frank Bauer, Bonn (DE); Chitoor Subramaniam, East Brunswick, NJ (US)

(73) Assignee: Creanova, Inc., Piscataway, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/493,908

(22) Filed: Jan. 28, 2000

(51) Int. Cl.$^7$ .................... C07C 255/13; C07C 69/66
(52) U.S. Cl. .................... 558/448; 560/186; 560/187
(58) Field of Search .................... 558/448; 560/186, 560/187

(56) References Cited

U.S. PATENT DOCUMENTS

| 2,527,533 A | * 10/1950 | Copenhaver | 260/615 |
| 4,410,733 A | * 10/1983 | Mangold et al. | 568/603 |
| 4,518,785 A | * 5/1985 | Eckhardt et al. | 549/453 |
| 4,808,595 A | 2/1989 | Hoffman, Jr. | 514/302 |

FOREIGN PATENT DOCUMENTS

JP 62890771 12/1986 ......... C07D/213/80

OTHER PUBLICATIONS

Ullmann'Encyclopedia of Industrial Chemistry, 5th Edition, VCH Verlagsgesellschaft, Weinbeim, vol. A1, pp. 36–38.
Hoaglin et al., JACS 71, 3468 (1949).
von der Brüggen et al., J. Org. Chem., 1988, 53, 2920–2925.
March, "Advanced Organic Chemistry", 3rd ed.. J. Wiley, 1985, pp. 670ff and pp. 484–487.
Imada et al., Kogyo Kagaku Zosshi (1969) 72(a), 2138–42.
Okaya et al., Makromol. Chem. (1970) 133, 227–239.
Rasmussen et al., Acta. Chem. Scand., 20, 1351 (1966).
Chevier et al., Agnew Chem. Int. Ed. Engl., 13, 1–10 (1974).
Olah, Friedel Crafts and Related Reactions, vol. I, (Interscience, 1963) pp. 230–567.
Benoit, R., "Synthesis and Study of Chiral NADH Models in the Thieno[2,3–b]pyridine Series", Journal Heterocyclic Chemistry, 26, 1595 (1989).
Schenone, P., et al., "Reaction of 2–Dimethylaminomethylene–1,3–diones with Dinucleophiles. VII. Synthesis of Ethyl and Methyl 2,4–Disubstituted 5–Pyrimidinecarboxylates", Journal Heterocyclic Chem., 27, 295 (1990).
Holzer, "N–1 Substituted Ethyl 4–Pyrazolecarboxylates: Synthesis and Spectroscopic Investigations", Journal Heterocyclic Chemistry 30, 865 (1993).
Kusumi et al., "Isolation, Structure and Synthesis of 4–Hydroxyisoxazole (Triumferol), A Seed Germination Inhibitor From an African Plant", Tetrahedron Letters, vol. 22, No. 36, pp. 3451–3454, (1981).
Genin, Michael, et al., "Nitrogen–Carbon Linked (Azolyphenyl) oxazolidinones with Potent Antibacterial Activity Against the Fastidious Gram–Negative Organisms Haemophilus Influenzae and Moraxella Catarrhalis", J. Med. Chemistry, 41, 5144–5147, (1998).
Bertz et al., "New Preparations of Ethyl 3,3–Diethoxypropionate and (Ethoxycarbonyl)malondialdehyde. Cu(I)–Catalyzed Acetal Formation from Conjugated Triple Bond", J. Org. Chem., 47, 2216–2217, (1982).
Von V. Prelog, "Zur Kenntnis Der Phenol–Synthese Aus β–Dicarbonyl–Verbindungen und Ketonen" Helvetica Chimica Acta, vol. XXXIV, Fasciculus I No. 27, (1951).
Reichardt, "Vilsmeier–Formylierung von Acetonitril", Synthesis, p. 538, (1970).
Bertz et al., "Synthesis of Biocyclo[3.3.1]Nonane Derivatives Under Physiological Conditions", Angew. Chem. Int. Ed. Engl. 21 No. 4 pp. 306–307 (1982).

\* cited by examiner

Primary Examiner—Rosalynd Keys
(74) Attorney, Agent, or Firm—Abelman, Frayne & Schwab

(57) ABSTRACT

A process directed to the preparation of 2-substituted and 2,2-disubstituted acetals of malondialdehyde from ortho formates and substituted vinyl ethers in the presence of an acidic catalyst.

32 Claims, No Drawings

PROCESS FOR PREPARING SUBSTITUTED ACETALS OF MALONDIALDEHYDE

FIELD OF THE INVENTION

The present invention relates to a process for preparing 2-substituted and 2,2-disubstituted acetals of malondialdehyde.

BACKGROUND OF THE INVENTION

Substituted acetals of malondialdehyde of the general formula (I):

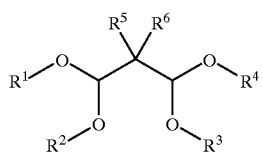

in which $R^1$, $R^2$, $R^3$ and $R^4$ are the same or different alkyl, cycloalkyl, aralkyl or aryl groups with up to 12 carbon atoms and in which $R^5$ and $R^6$ represent independently of each other H, alkyl, cycloalkyl, aralkyl, aryl, COOH, COONa, COOR, CHO, C(OR)$_2$, CN, CONH$_2$, CONHR, or CONR$_2$, with the proviso that $R^5$ and $R^6$ cannot both be H, alkyl, cycloalkyl or aralkyl, are valuable building blocks for the synthesis of heterocycles.

The compounds of general formula I can be easily hydrolyzed to the respective 2-substituted and 2,2-disubstituted free malondialdehydes of general formula II where $R^5$ and $R^6$ are as described above:

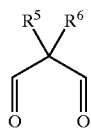

Accordingly, they have to be regarded as precursors for any product the synthesis of which requires the use of the free aldehydes of general formula II.

While the substituted malondialdehydes of general formula II are normally more stable toward polymerization than the unsubstituted malondialdehyde, they are thermally unstable as indicated, for example, by losses of 41% on distillation of ethoxycarbonyl malondialdehyde under very mild conditions (Bertz, S. H., Dabbagh, G., Cotte, J. Org. Chem. 1982, 47, 2216). Since handling-hazards and product losses, as well as a potential contamination of the reaction mixtures with polymeric material result from using the compounds of general formula II for the synthesis of heterocycles, and since the compounds of general formula I can be stored even above room temperature for extended periods of time, it is advantageous to generate the substituted malondialdehydes of general formula II from the malondialdehyde acetals of general formula I either just prior to their use or, preferably, in situ, especially under commercial conditions.

The compound 2-ethoxycarbonyl-malondialdehyde has found an especially broad range of applications, for example, in the synthesis of pyridine derivatives (JP 61,289,077), pyrimidines (Schenone, P., Sansebastiano, L., Mosti, L., J. Heterocycl. Chem. 1990, 27 (2), 295), pyrazoles (Holzer, W., Seiringer, G., J. Heterocycl. Chem. 1993, 30, 865), isoxazoles (Kusumi, T. et al., Tetrahedron Letters 22 (1981), 36, 3451), phenolic compounds (Prelog, V., Wuersch, J., Koenigsbacher, K., Helv. Chim. Acta 1951, 34, 258; Bertz, S. H., Dabbagh, G., Angew. Chem. Int. Ed. Engl. 1982, 21, 306) and pharmaceuticals (U.S. Pat. No. 4,808,595; Genin, M., J. et al. J. Med. Chem. 1998, 41, 5144). This broad utility is at least partially due to the availability of this compound by the condensation of. 3,3-diethoxypropionate with ethyl formate in the presence of base (Bertz, S. H., Dabbagh, G., Cotte, P., J. Org. Chem. 1982, 47, 2216). Besides providing the free aldehyde instead of a diacetal, this approach suffers from several major drawbacks, such as the expense of 3,3-diethoxypropionate, the difficulty encountered in handling NaH, which is the starting material and the formation of wastewater.

Ethyl-2-dimethoxymethyl-3,3-dimethoxy-propionate can be prepared by the reaction of malondialdehyde bis-dimethylacetal with carbonochloridic acid ethyl ester. However, this approach has to be regarded as being solely a laboratory synthesis since it requires the handling of such hazardous materials as potassium and diethylether. Further, the use of liquid ammonia as the reaction medium is very costly under commercial conditions.

The situation with respect to other 2-substituted malondialdehyde-derivatives is similar. Whereas, for example, 2-cyano-3-dimethylamino-acrolein is a stable precursor for 2-cyano-malondialdehyde, its synthesis via Vilsmeier-formylation of acetonitrile (Reichardt, G., Kerrner, W. D., Synthesis 1970, 538) leads to excessive formation of phosphorous-contaminated wastewater besides which the yield is only 32% , referred to DMF. Also, this approach is fairly specific and gives dimethylamine on hydrolysis of the malondialdehyde-precursor.

While there are some applications for the compounds of general formula I, such as the synthesis of substituted pyridines (Benoit, R. et al., J. Heterocycl. Chem. 1989, 26, 1595), their use is largely limited by their availability. Thus, a need exists for a general process that affords 2-substituted and 2,2-disubstituted acetals of malondialdehydes of general formula I from easily available starting materials without the drawback of requiring several steps and/or the stoichiometric formation of salts and/or the formation of excessive amounts of wastewater.

By the process of the present invention ready access is provided to the compounds of general formula I by the addition of ortho formates to 2-substituted and 2,2-disubstituted vinylethers, thereby avoiding the above-noted disadvantages.

SUMMARY OF THE INVENTION

The present invention provides a process for the preparation of 2-substituted and 2,2-disubstituted acetals of malondialdehyde of general formula I:

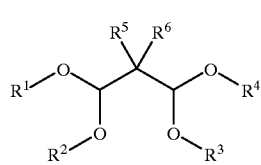

in which $R^1$, $R^2$, $R^3$ and $R^4$ are the same or different alkyl groups, cycloaliryl groups, aralkyl groups or aryl groups with up to 12 carbon atoms and in which $R^5$ and $R^6$ represent independently of each other H, alkyl, cycloalkyl, aralkyl, aryl, COOH, COONa, COOR, CHO, C(OR)$_2$, CN, CONH$_2$, CONHR or CONR$_2$, with the proviso that R$^5$ and R$^6$ cannot both be H, alkyl, cycloalkyl or aralkyl, by reacting compounds of general formula III:

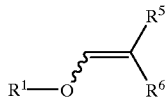

III and ortho formates of general formula IV:

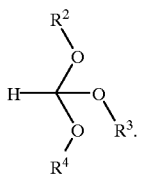

IV

DETAILED DESCRIPTION OF THE INVENTION

The present invention provides a process for preparing 2-substituted and 2,2-disubstituted acetals of malondialdehyde of general formula I:

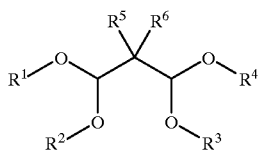

I in which R$^1$, R$^2$, R$^3$ and R$^4$ are the same or different alkyl groups, cycloalkyl groups, aralkyl groups or aryl groups with up to 12 carbon atoms and in which R$^5$ and R$^6$ represent independently of each other H, alkyl, cycloalkyl, aralkyl, aryl, COOH, COONa, COOR, CN, CHO, C(OR)$_2$, CONH$_2$, CONHR, or CONR$_2$, with the proviso that R$^5$ and R$^6$ cannot both be H, alkyl, cycloalkyl or aralkyl.

Upon hydrolysis of the compounds of general formula I to the free aldehydes, it is normally advantageous to avoid the generation of a mixture of alcohols. In a preferred embodiment of the process of the invention, the groups R$^1$, R$^2$, R$^3$ and R$^4$ are therefore identical.

It has been found that this is achieved in a simple manner and that 2-substituted and 2,2-disubstituted acetals of malondialdehyde of general formula I are obtained advantageously when a vinylether of general formula III:

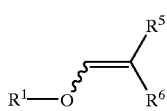

III in which R$^1$, R$^5$ and R$^6$ are as defined above, is reacted with an ortho formate of general formula IV:

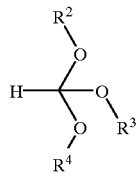

IV in which R$^2$, R$^3$ and R$^4$ are as defined above.

In the absence of a catalyst, the above reaction is normally extremely slow. It is, therefore, advantageous to conduct the reaction in the presence of a catalyst. Acidic catalysts, especially strong Lewis acids, give superior reactivities and selectivities. Examples of such catalysts are SnCl$_4$, SnCl$_3$Ph, AlCl$_3$, BBr$_3$, SbF$_5$, and ZnCl$_2$, FeCl$_3$ as well as BF$_3$ have been found to be especially selective and reactive homogeneous catalysts. Since homogeneous, as well as heterogeneous catalysts, such as acidic Al$_2$O$_3$ or montmorillonites, have been found to increase the reaction rate, in a preferred embodiment of the process according to the present invention, the reaction is carried out continuously using a fixed catalyst bed. A fixed bed catalyst does not have to comprise a single compound or a single mineral. The use of homogeneous catalysts, especially Lewis acids like FeCl$_3$ on a suitable support, such as SiO$_2$, and commercially available catalysts, such as Envirocat EPZG sold by Contract Chemicals Ltd. of Prescot, Merceyside, United Kingdom have been found to produce advantages with respect to reactivities and handling properties.

The amount of catalyst required to give desirable reaction rates has been found to cover a broad range and depends to a great extent on the nature of the catalyst, as well as the substitution pattern of the starting materials, particularly in the edge of R$^5$ and R$^6$. Normally, catalyst-concentrations below 0.00001 w/w-% referring to the compounds of general formula III, lead to reaction-times of several days even when using highly reactive Lewis acids. On the other hand, especially if the process according to the invention is conducted continuously using a heterogeneous catalyst and provided the reaction mixture is sufficiently diluted, it has been found advantageous to use catalyst concentrations as high as 5000 w/w-% referring to the compounds of general formula III. When using homogeneous catalysts, concentrations in the range of about 0.1% to about 30%, preferably in the range of about 1% to about 15%, yielded commercially acceptable reaction rates in most instances.

At least in certain instances, the preferred catalysts according to the invention, for example, BF$_3$, Al$_2$O$_3$ and FeCl$_3$ are slowly deactivated under the reaction conditions. On the other hand, a high reactivity of the catalyst at relatively low temperatures is highly desirable in view of the economics of the process. In a preferred embodiment of the process according to the present invention, the catalyst or mixture of catalysts is, therefore, continuously or semi-continuously fed to the other components of the reaction mixture. The catalyst can be fed in pure form or in the form of a solution. Feeding a solution of the catalyst has the advantage of allowing for the use of a metering pump.

Even when using relatively mild Lewis acids, and especially when using very strong Lewis acids or strong protic acids as the catalyst, the ortho fonnates of general formula IV quickly decompose if the reaction temperature exceeds 220° C. On the other hand, the reaction rates at temperatures below –100° C. are too slow to be commercial interest. The best compromise between sufficiently high reaction rates and acceptable losses of the ortho formates of general formula IV depends very much on the type of Lewis acid used as the preferred catalyst according to the invention. Acceptable yields based upon the converted ortho formates of general formula IV are generally achieved in a temperature range between about −30° C. and about 100° C., with a temperature range of between about −15° C. to about 50° C. being especially preferred, and a range of about −10° C. to about 15° C. being most preferred.

The use of a co-catalyst comprising a precious metal from the group Ru, Rh, Pd, Os, Ir and Pt was found to be advantageous in those instances where the compounds of general formula I are either not formed at a reasonable rate or are not formed at all. In a preferred embodiment of the process of the present invention such co-catalysts exhibit an oxidation state >0. Especially preferred co-catalysts are $Pt^{2+}$, $Pt^{4+}$, $Pd^{2+}$ and $Pd^{4+-}$ and complexes such as $PtCl_2(ACN)_2$, $PtCl_2(SEt_2)_2$, $PdCl_2(ACN)_2$, $Pd(ACN)_4$, etc. In order to stabilize these co-catalysts, it has been found advantageous to add between about 1 ppm and about 10% of an oxidant, such as $Cu^{2+}$, $Fe^{3+}$ 1,4-benzoquinone or di-tert.-butylperoxide to the reaction mixture.

As described previously, the ortho formates of general formula IV tend to partially decompose on heating in the presence of Lewis acids. Maximum yields of products of general formula I when referring to the ortho formates of general formula IV are achieved if the ortho formates are continuously or semi-continuously fed to the other components of the reaction mixture. Also, the yields when referring to the converted compounds of general formula III and the conversions of the compounds of general formula III are increased by using an up to 10-fold molar excess, preferably about a 1.2-fold to about a 3-fold excess, of the ortho formates of general formula IV over the compounds of general formula III. Surprisingly, the yields of the compounds of general formula I are generally increased if low-boiling by-products, such as alkanols and alkylformates are removed during the reaction. This removal of low-boilers is especially preferred if one of the above precious metal co-catalysts is used. In a preferred embodiment of the process of the present invention, the low-boiling impurities which are formed are, therefore, continuously removed by fractional distillation, preferably in vacuo.

The compounds of general formula III are sensitive toward polymerization, i.e., they have a tendency to form polymers. Therefore, a major concern when reacting the compounds of general formula III and IV is the heat of reaction that can potentially be evolved on polymerization of the compounds of general formula III. While such polymerization was not observed under the preferred conditions of the process according to the present invention, precautions must be taken in order to guarantee safety, especially if the reaction is run batch-wise. It has been found that the reaction can be conducted in a safe manner by using a sufficient excess of the compound of general formula IV, or by sufficiently diluting the reaction mixture with an appropriate solvent. Ideally, such solvent does not react with any of the other components of the reaction mixture. Preferred solvents, therefore, are hydrocarbons like toluene, cyclohexane, octane, etc., or ethers like polyethylene glycol ethers or methyl-tert.-butylether. Due to the fact that certain logses of the ortho formates of general formula IV cannot be totally avoided under the preferred reaction conditions, a dilution of the reaction mixture with a solvent is preferred over the initial addition of a sufficient amount of the ortho formates of general formula IV to prevent a potential overheating of the reaction mixture due to polymerization of the compounds of general formula III. Naturally, suitable stabilizers can be added to the reaction mixture, preferably through already stabilized starting materials, in order to avoid losses of starting materials and/or products due to polymerization. Examples of such stabilizers are MEHQ, 2,4-di-tert.-butyl-p-cresol, hydroquinone monomethylether, hydroquinone, etc. Since the preferred catalysts according to the invention tend to be deactivated under the reaction conditions, it is, however, not absolutely necessary to dilute the system. Any polymerization of the compounds of general formula III heats up the reaction mixture leading to an increased catalyst breakdown. In this sense, the process according to the invention is intrinsically safe. Consequently, in a preferred embodiment of the invention, dilution of the system is reduced to a minimum in order to maximize the space time yield.

The isolation of the products of general formula I can be easily achieved by fractional distillation. Due to the lower boiling point of non-converted starting materials of general formulas III and IV as compared to the product of general formula I, the starting materials can be reused after their separation from the product. For the further purification of the compounds of general formula I standard procedures such as crystallization, column chromatography, etc. can be used. In a preferred embodiment of the process according to the invention, the products of general formula I are further purified by distillation.

It is a special advantage of the process according to the present invention that no significant amounts of byproducts with a boiling point similar to that of the products of It is a general formula I are formed. Therefore, the compounds of general formula I are obtained in a high degree of purity, for example 99%, by short-path distillation of the crude product of formula I.

Depending on the type of acidic catalyst used, it can be advantageous to either remove it mechanically, for example by filtration, and/or to neutralize the reaction mixture or the crude product that remains after removal of the low-boilers and/or the starting materials of general formulas III and IV with a suitable base, for example $NaOCH_3$, NaO-tert.-butyl, NaOH, $NEt_3$, $Na_2CO_3$, $NaHCO_3$, etc. While the resulting salts can principally remain in the crude product, better yields are usually achieved if they are mechanically removed prior to distillation.

Another possibility for removing the acidic catalyst from the crude reaction mixture, comprises bringing it into contact with water, or preferably an aqueous solution of a base, such as sodium hydroxide, and subsequently removing the aqueous phase. While such alkaline washing allows for total removal of acidity, substantial amounts of wastewater are formed, and the acidic catalyst is lost.

Provided the preferred catalysts according to the invention are sufficiently mild-for example, in the case of $FeCl_3$—a neutralization prior to the distillative isolation of the products of general formula I is not necessary. Therefore, in a preferred embodiment of the invention, the reaction mixture is worked up by recovering any non-converted starting no materials of general formulas m and IV, followed by a distillation of the product of general formula I. In order to minimize the distillation temperature and the residence time, a continuous distillation process, preferably using a short-path evaporator or wiped-film evaporator, as well as the application of vacuum, is advantageous.

As mentioned earlier, the products of general formula I can easily be hydrolyzed to the free aldehydes of general formula II. In order to convert the so-formed free aldehydes to secondary products like heterocycles, it is not necessary to isolate them. It has, in fact, been found that higher yields of secondary products are achieved, if the aldehydes of general formula II are generated from the compounds of general formula I in situ. This finding is apparently due to the sensitivity of the compounds of general formula II under the reaction conditions.

Having described the present invention, reference will now be made to certain examples, which are provided solely for purposes of illustration and are not intended to be limiting.

EXAMPLES

Example 1

Methyl-3,3-dimethoxy-2-dimethoxymethylpropionate

To a stirred mixture of 17.7 g methyl-trans-3-methoxyacrylate and 32.3 g trimethyl ortho formate was added 1.0 g $FeCl_3$. The mixture was heated to 40° C. for 24 hours, cooled to room temperature and 5.00 g anhydrous sodium carbonate were added. After stirring for 2 hours, the mixture was filtered and the filter-cake washed with trimethyl ortho formate. Fractional distillation gave 12.9 g colorless liquid (76.5% of theoretical based on converted methyl-trans-3-methoxyacrylate) of boiling point 100° C./4 mm Hg. A GC-analysis of the liquid revealed an assay of >99% (FID-detection).

Example 2

Methyl-3,3-dimethoxy-2-dimethoxymethylpropionate

To a stirred mixture of 17.7 g methyl-trans-3-methoxyacrylate and 32.3 g trimethyl ortho formate was added 0.4 g $FeCl_3$. The mixture was heated to 40° C. for 24 hours, whereby 0.2 g $FeCl_3$ were added every 6 hours. After cooling to room temperature, 5.00 g anhydrous sodium carbonate were added and the reaction mixture was stirred for 2 hours. Filtering, washing the filter-cake washed with trimethyl ortho formate and fractional distillation gave 13.5 g colorless liquid (80% of theoretical based on converted methyl-trans-3-methoxyacrylate) of boiling point 100° C./4 mm Hg. GC-analysis of the liquid revealed an assay of >99% (FID-detection).

Example 3

Methyl-3,3-dimethoxy-2-dimethoxymethylpropionate

To a stirred mixture of 17.7 g methyl-trans-3-methoxyacrylate and 32.3 g trimethyl ortho formate was added 1.0 g $PhSnCl_3$. The mixture was heated to 60° C. for 24 hours, cooled to room temperature and 5.00 g anhydrous sodium carbonate were added. After stirring for 2 hours, the mixture was filtered and the filter-cake washed with trimethyl ortho formate. Fractional distillation gave 11.6 g colorless liquid (69% of theoretical based on converted methyl-trans-3-methoxyacrylate) of boiling point 1000° C./4 mm Hg, A GC-analysis of the liquid revealed an assay of >99% (FID-detection).

Example 4

Methyl-3,3-dimethoxy-2-dimethoxymethylpropionate

To a stirred mixture of 116.0 g methyl-trans-3-methoxyacrylate and 530.0 g trimethyl ortho formate were added 5.0 g $FeCl_3$. The mixture was heated to 35° C. for 30 hours with an additional 1.0 g $FeCl_3$ being added every 6 hours. The mixture was cooled to room temperature and neutralized by addition of 30% sodium methylate solution. After stirring for 2 hours, 30.0 g PEG-dimethylether (mg=1000) were added. The trimethyl ortho formate excess was recovered by fractional distillation. Flash-distillation of the remaining material gave 155.4 g colorless liquid (80% of theoretical based on converted methyl-trans-3-methoxyacrylate) of boiling point 100° C./4 mm Hg. A GC-analysis of the liquid revealed an assay of >99% (FID-detection).

Example 5

Methyl-3 , 3-dimethoxy-2-dimethoxymethylpropionate

To a stirred mixture of 35.4 g of methyl-trans-3-methoxyacrylate were added 0.2 g $FeCl_3$. The mixture was heated to 60° C. and 64.6 g trimetlyl ortho formate and—separately—2.0 g $FeCl_3$ were added over a period of 12 hours. The mixture was stirred for another 12 hours, cooled to room temperature and 7.0 g anhydrous sodium carbonate were added. After stirring for 2 hours, the mixture was filtered and the filter-cake washed with 20.0 g trimethyl ortho formate. Fractional distillation gave 17.3 g colorless liquid (70% of theoretical yield based on converted trimethyl ortho formate) of boiling point 100° C./4 mm Hg. GC-analysis of the liquid revealed an assay of 99% (FID-detection).

Example 6

Ethyl-3,3-diethoxy-2-dimethoxyethylpropionate

To a stirred mixture of 48.00 g ethyl-3-ethoxyacrylate (mixture of isomers; prepared from ethyl bromoacetate, ethyl ortho formate and Zn) and 148.00 g triethyl ortho formate were added 4.00 g $FeCl_3$. The mixture was heated to 45° C., overnight, cooled to room temperature and 15.0 g anhydrous sodium carbonate were added. After stirring for 2 hours, the mixture was filtered and the filter-cake washed with triethyl ortho formate. Removal of residual starting materials by heating to 100° C./2 mm Hg gave 22.1 g of a yellow residue (68% of theoretical yield based on ethyl-3-ethoxyacrylate). The residue was identified as ethyl-3,3-diethoxy-2-dimethoxyethylpropionate by 1H- and 13C-NMR. A GC-analysis revealed an assay of 97% (FID-detection).

Example 7

2-Methyl-3 ,3-dimethoxy-2-dimethoxymethyl-methylpropionate

To a stirred mixture of 20.6 g 3-methoxy-methylmethacrylate (mixture of isomers; prepared from methyl-2,3-dibromo-2-methyl-propionate and sodium methylate) and 150.0 g trimethiyl orthio formate were added 2.00 g $FeCl_3$. The mixture was heated to 40° C. for 48 hours, cooled to room temperature and 15.00 g anhydrous sodium carbonate was added. After stirring for 2 hours, the mixture was filtered and the filter-cake washed with trimefflyl ortho formate. GC/MS and GCIIR-analysis of the filtered reaction mixture revealed the formation of 2-methyl-3,3-dimethoxy-2-dimethoxymethylpropionate. The yield was determined to be 70% of theoretical yield based on converted 3-methoxy-methyl methacrylate (FID-detection).

Example 8

3,3-Dimethoxy-2-dimethoxymethyl-propionitrile

To a stirred mixture of 2.0 g 3-methoxy-acrylonitrile and 4.0 g trimethyl ortho formate were added 2.0 g $BF_3*OEt_2$. The mixture was stirred at room temperature for 48 hours and afterwards neutralized with 30 w/w-% sodium methylate solution. GC-analysis of the filtered reaction mixture did not reveal any formation of 3,3-dimethoxy-2-dimethoxymethyl-propionitrile (FID-detection).

Example 9

3,3-Dimethoxy-2-dimethoxymethyl-propionitrile

To a stirred mixture of 5.0 g 3-methoxy-acrylonitrile and 10.0 g trimethyl ortho formate were added 2.5 g $BF_3*OEt_2$ and 1.0 g $PdCl_2(ACN)_2$. The mixture was stirred at room temperature for 18 hours and afterwards neutralized with 30 w/w-% sodium methylate solution. GC-analysis of the filtered reaction mixture revealed the formation of 3,3-dimethoxy-2-dimethoxymethyl-propionitrile in 55% of theoretical yield based on converted 3-metlioxyacrylonitrile (FID-detection).

Example 10

2-Chloro-1,1,3,3-tetramethoxypropane

To a stirred mixture of 1.50 g 3-methoxyvinyl chloride (mixture of isomers, prepared from 2,2-dichloroethylmethylether and KOH) were added 0.20 g $FeCl_3$. The mixture was heated to 35° C. and 30.0 g trimethyl ortho formate and —separately —0.40 g $FeCl_3$ were added over a period of 8 hours. The mixture was stirred for another 20 hours, cooled to room temperature and 3.0 g anhydrous sodium carbonate were added. After stirring for 2 hours, the mixture was filtered and the filter-cake washed with trimethyl ortho formate. Analysis of the filtrate by GC/MS and GC/IR revealed the formation of 2-chloro-1,1,3,3-tetramethoxypropane in 65% yield referred to converted 3-methoxyvinyl chloride.

Example 11

Methyl-3,3-dimethoxy-2-dimethoxy methylpropionate

The procedure of example 4 was followed except that the molar ratio of TMOF to methyl-trans-3-methoxyacrylate was lowered to 2:1, the reaction temperature was lowered to 7° C., 4.05 mole-% $FeCl_3$ with reference to TMOF was used as the catalyst and the reaction time was limited to 20.5 hours. By this means, an isolated yield of >90% based on converted methyl-trans-3-methoxyacrylate and 53% based on converted trimeethyl orthoformate was achieved respectively.

What is claimed is:

1. A process for preparing 2-substituted and 2,2disubstituted acetals of malondialdehyde of general forms I:

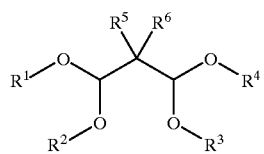

in which $R^1$, $R^2$, $R^3$ and $R^4$ are selected from the group consisting of the same or different alkyl groups, cycloalkyl groups, aralky groups or aryl groups with up to 12 carbon atoms and which $R^5$ is a member selected from the group consisting of COOH, COONa, COOR, CHO, $C(OR)_2$, CN, $CONH_2$, CONHR, or $CONR_2$, and $R_6$ is independently, selected from the group consisting of H, alkyl, cycloallyl, aralkyl, aryl, COOH, COONa, COOR, CHO, $C(OR)_2$, CN, $CONH_2$, CONHR or $CONR_2$ with the proviso that $R^5$ and $R^6$ cannot both=H, alkyl, cycloalkyl, aryl or aralky, which comprises reacting a compound of general formula III:

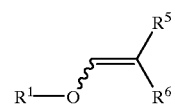

with an ortho formate of general formula IV:

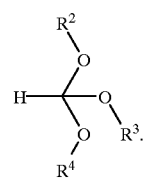

in the presence of an acidic homogeneous or heterogeneous catalyst having a concentration of from about 0.00001 w/w-% to about 5000 w/w-% of compound III at a temperature in the range of about –100° C. to about 220° C.

2. The process of claim 1, wherein the reaction is conducted in the presence of a homogeneous catalyst at a concentration of about 0.1 w/w% to about 30 w/w% with reference to the compound of general formula III.

3. The process of claim 2, wherein the catalyst concentration is from about 0.1 w/w% to about 15 w/w% of compound III.

4. The process of claim 1, wherein the catalyst is selected from the group consisting of Lewis acids and mixtures of Lewis acids.

5. The process of claim 4, wherein the Lewis acids are selected from the group consisting of $SnCl_4$, $FeCl_3$ and $BF_3$, and mixtures thereof.

6. The process of claim 5, wherein a mixture of $SnCl_4$ and $FeCl_3$ is used as the catalyst system.

7. The process of claim 1, wherein the reaction is conducted in the presence of a co-catalyst selected from the group consisting of Ru, Rh, Pd, Os, Ir or Pt.

8. The process of claim 1, wherein the precious metal exhibits an oxidation state >0.

9. The process of claim 8, wherein the precious metal compound is stabilized by the addition of an oxidant selected from the group consisting of $Cu^{2+}$, $Fe^{3+}$, 1,4-benzoquinone or di-tert, -butyl-peroxide to the reaction mixture.

10. The process of claim 1, wherein the catalyst is continuously or semi-continuously fed to the other components of the reaction mixture.

11. The process of claim 1, wherein the catalyst or the co-catalyst, or both, are continuously or semi-continuously fed to the other components of the reaction mixture.

12. The process of claim 1, wherein a polymerization inhibitor is added to the reaction mixture.

13. The process of claim 1, wherein the reaction is carried out in the range of about −30° C. to about 100° C.

14. The process of claim 13, wherein the reaction is carried out in the range of about −15° C. to about 50° C.

15. The process of claim wherein the reaction is carried out in the range of about −10° C. to about 15° C.

16. The process of claim 1, wherein up to about 10-fold molar excess of the ortho formate of general formula IV is employed compared to the compound of general formula III.

17. The process of claim 16, wherein about a 1.2 to about 3 fold molar excess of the ortho formate is employed compared to the compound of general formula III.

18. The process of claim 1, wherein the ortho formate of general formula IV is added to the other components of the reaction mixture.

19. The process of claim 16, wherein the ortho formate excess is recovered and recycled for use in the process.

20. The process of claim 17, wherein the ortho formate excess is recovered and recycled for use in the process.

21. The process of claim 17, wherein the ortho formate excess is added to the other components of the reaction mixture.

22. The process of claim 1, wherein the reaction is carried out in the presence of a solvent or a mixture of solvents which neither react to a significant extent with the starting materials nor with the products.

23. The process of claim 22, wherein the solvent is a hydrocarbon.

24. The process of claim 23, wherein the hydrocarbon is selected from the group consisting of toluene, cyclohexane, ethers, and chlorinated hydrocarbons.

25. The process of claim 1, wherein low-boiling reaction byproducts which are formed are continuously removed during the reaction.

26. The process of claim 25, wherein low-boiling alkanols and lower alkyl esters are removed by fractional distillation.

27. The process of claim 1, wherein the 2-substituted and 2,2-disubstituted acetals of malondialdehyde are isolated by distillation.

28. The process of claim 27, wherein the 2-substituted and 2,2-disubstituted acetals of malondialdehyde are isolated by fractional distillation.

29. The process of claim 1, wherein the, catalyst is neutralized prior to distillation.

30. The process of claim 1, wherein the catalyst is removed from the reaction mixture by filtration.

31. The process of claim 1, wherein the reaction mixture is worked up by contacting it with an aqueous solution of a base with subsequent removal of the aqueous phase.

32. The process of claim 1, wherein the 2-substituted and 2,2-disubstituted acetals of malondialdehyde of general formula I are hydrolyzed to the free aldehydes of general formula II:

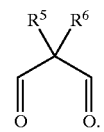

* * * * *